(12) United States Patent
Chakravarty et al.

(10) Patent No.: US 9,642,909 B2
(45) Date of Patent: May 9, 2017

(54) **PHARMACEUTICAL COMPOSITIONS COMPRISING ATTENUATED *PLASMODIUM* SPOROZOITES AND GLYCOLIPID ADJUVANTS**

(71) Applicants: Sanaria Inc., Rockville, MD (US); The Rockefeller University, New York, NY (US)

(72) Inventors: Sumana Chakravarty, Derwood, MD (US); Stephen L. Hoffman, Gaithersburg, MD (US); Moriya Tsuji, New York, NY (US)

(73) Assignees: Sanaria Inc., Rockville, MD (US); The Rockefeller University, New York, NY (US)

( * ) Notice: Subject to any disclaimer, the term of this patent is extended or adjusted under 35 U.S.C. 154(b) by 0 days.

(21) Appl. No.: 15/046,575

(22) Filed: Feb. 18, 2016

(65) Prior Publication Data
US 2016/0158351 A1 Jun. 9, 2016

Related U.S. Application Data

(60) Division of application No. 14/065,012, filed on Oct. 28, 2013, now Pat. No. 9,278,125, which is a (Continued)

(51) Int. Cl.
*A61K 39/015* (2006.01)
*A61K 39/39* (2006.01)
(Continued)

(52) U.S. Cl.
CPC ............ *A61K 39/39* (2013.01); *A61K 9/0019* (2013.01); *A61K 9/0021* (2013.01);
(Continued)

(58) Field of Classification Search
None
See application file for complete search history.

(56) References Cited

U.S. PATENT DOCUMENTS 4,850,305 A 7/1989 Georgi et al.
RE35,348 E 10/1996 Georgi
(Continued)

FOREIGN PATENT DOCUMENTS

CN 1142887 A 12/1995
CN 1213497 A 10/1997
(Continued)

OTHER PUBLICATIONS

Alonso, PL et al., Efficacy of the RTS,S AS02A vaccine against *Plasmodium falciparum* infection and disease in young African children: randomized controlled trial. *Lancet* 364:1411-1420 (2004).

(Continued)

*Primary Examiner* — Padma V Baskar
(74) *Attorney, Agent, or Firm* — Sterne, Kessler, Goldstein & Fox P.L.L.C.

(57) ABSTRACT

Disclosed herein are pharmaceutical compositions comprising *Plasmodium* sporozoite-stage parasites and compatible glycolipid adjuvants useful in vaccines for preventing or reducing the risk of malaria. In particular, human host range *Plasmodium* and analogues of α-galactosylceramide (α-GalCer), a ligand for natural killer T (NKT) cells, are combined in pharmaceutical compositions, which are useful as vaccines against malaria. Methods of use are also provided.

16 Claims, 1 Drawing Sheet

Related U.S. Application Data continuation of application No. 13/470,128, filed on May 11, 2012, now abandoned.

(60) Provisional application No. 61/485,092, filed on May 11, 2011.

(51) Int. Cl.
   *A61K 9/00* (2006.01)
   *A61K 39/00* (2006.01)
(52) U.S. Cl.
   CPC ...... *A61K 39/015* (2013.01); *A61K 2039/522* (2013.01); *A61K 2039/54* (2013.01); *A61K 2039/55511* (2013.01)

(56) References Cited

U.S. PATENT DOCUMENTS

| | | | |
|---|---|---|---|
| 5,766,597 | A | 6/1998 | Paoletti et al. |
| 5,983,557 | A | 11/1999 | Perich et al. |
| 7,122,179 | B2 | 10/2006 | Kappe et al. |
| 7,229,627 | B2 | 6/2007 | Hoffman et al. |
| 7,534,434 | B2 | 5/2009 | Tsuji et al. |
| 7,550,138 | B1 | 6/2009 | Waters et al. |
| 7,923,013 | B2 | 4/2011 | Tsuji et al. |
| 8,043,625 | B2 | 10/2011 | Sim et al. |
| 8,163,290 | B2 | 4/2012 | Tsuji et al. |
| 8,268,969 | B2 | 9/2012 | Wong et al. |
| 8,367,810 | B2 | 2/2013 | Sim et al. |
| 8,802,919 | B2 | 8/2014 | Hoffman et al. |
| 8,821,896 | B2 | 9/2014 | Sim et al. |
| 8,992,944 | B2 | 3/2015 | Sim et al. |
| 9,241,982 | B2 | 1/2016 | Sim et al. |
| 9,278,125 | B2 | 3/2016 | Chakravarty et al. |
| 2005/0208078 | A1 | 9/2005 | Hoffman et al. |
| 2005/0220822 | A1 | 10/2005 | Hoffman et al. |
| 2005/0233435 | A1 | 10/2005 | Kappe et al. |
| 2007/0169209 | A1 | 7/2007 | Hoffman et al. |
| 2012/0156245 | A1 | 6/2012 | Hoffman et al. |
| 2012/0288525 | A1 | 11/2012 | Chakravarty et al. |
| 2012/0328645 | A1 | 12/2012 | Hoffman et al. |
| 2013/0224250 | A1 | 8/2013 | Sim et al. |
| 2013/0251750 | A1 | 9/2013 | Sim et al. |
| 2015/0313980 | A1 | 11/2015 | Janse et al. |
| 2016/0175417 | A1 | 6/2016 | Sim et al. |
| 2016/0216276 | A1 | 7/2016 | Felgner et al. |

FOREIGN PATENT DOCUMENTS

| | | |
|---|---|---|
| GB | 1594721 A | 5/1978 |
| JP | 57156421 | 9/1982 |
| JP | 7-289119 | 7/1995 |
| WO | WO 91/16814 A1 | 11/1991 |
| WO | WO 92/11760 | 7/1992 |
| WO | WO 95/26633 | 10/1995 |
| WO | WO 00/74478 A1 | 12/2000 |
| WO | WO 03/087322 A2 | 10/2003 |

OTHER PUBLICATIONS

Beier, J.C., "Malaria Parasite Development in Mosquitoes," *Annu. Rev. Entomol.* 43:519-43 (1998).
Belnoue, E., et al., "Protective T Cell Immunity Against Malaria Liver Stage After Vaccination with Live Sporozoites Under Chloroquine Treatment," *The Journal of Immunology* 172:2487-2495, The American Association of Immunologists, United States (2004).
Breman, J.G., et al., "Defining and defeating the intolerable burden of malaria III. Progress and perspectives," *Am. J. Trop. Med. Hyg.* 77(Suppl 6):vi-xi, The American Society of Tropical Medicine and Hygiene, United States (2007).
Chattopadhyay et al., "The Effects of radiation on the safety and protective efficacy of an attenuated *Plasmodium yoelii* sporozoite malaria vaccine," *Vaccine* 27:3675-3680 (Jun. 2009).
Clyde, D.F., "Immunity to falciparum and vivax malaria induced by irradiated sporozoites: a review of the University of Maryland studies, 1971-75," *Bulletin of the World Health Organization* 68 (Suppl.):9-12, World Health Organization, Switzerland (1990).
Daubenberger, C.A., "First clinical trial of purified, irradiated malaria sporozoites in humans," *Expert Rev. Vaccines* 11(1):31-33, Expert Reviews Ltd, England (2012).
Doolan, D.L., and Hoffman, S.L., "The Complexity of Protective Immunity Against Liver-Stage Malaria," *The Journal of Immunology* 165:1453-1462, The American Association of Immunologists, United States (2000).
Edelman, R., et al., "Long-Term Persistence of Sterile Immunity in a Volunteer Immunized with Xlrradiated *Plasmodium falciparum* Sporozoites," *The Journal of Infectious Diseases* 168:1066-1070, Infectious Diseases Society of America, United States (1993).
Editorial. "Malaria, 2010: more ambition and accountability please," *The Lancet* 375:1407, Lancet Publishing Group, England (Apr. 2010).
Engelmann, S., et al., "Transgenic *Plasmodium berghei* sporozoites Expressing β-galactosidase for Quantification of Sporozoite Transmission," *Mol Biochem Parasitol.* 146(1): 30-37, Elsevier, Netherlands (2006).
Epstein, J.E. et al., "Malaria vaccines: are we getting closer?" *Curr. Opin. Hol. Ther.* 9(1):12-24 (2007).
Herrington, D.A., "Safety and immunogenicity in man of a synthetic peptide malaria vaccine against *Plasmodium falciparum* sporozoites," *Nature* 328:257-259, Nature Publishing Group, England (1987).
Herrington, D., et al., "Successful Immunization of Humans With Irradiated Malaria Sporozoites: Humoral and Cellular Responses of the Protected Individuals," *Am. J. Trop. Med. Hyg.* 45(5):539-547, The American Society of Tropical Medicine and Hygiene, United States (1991).
Hoffman, S.L., et al.,"Sporozite Vaccine Induces Genetically Restricted T Cell Elimination of Malaria from Hepatocytes,"*Science* 244:1078-1081, American Association for the Advancement of Science, United States (1989).
Hoffman, S.L., et al., "Protection of Humans against Malaria by Immunization with Radiation-Attenuated *Plasmodium falciparum* Sporozoites," *The Journal of Infectious Diseases* 185:1155-1164, The Infectious Diseases Society of America, United States (2002).
Hoffman, S.L., et al., "Development of a metabolically active, non-replicating sporozoite vaccine to prevent *Plasmodium falciparum* malaria," *Human Vaccines* 6:97-106, Landes Bioscience, United States (Jan. 2010).
Jiang, J-B., et al., "Induction of retarded exoerythrocytic schizonts by chloroquanide resulting in delayed parasitaemia of *Plasmodium inui* in *Macaca mulatta*," *Acta Pharmacologica. Sinica* 11(3):272-274, Shanghai Institute of Materia Medica (1990), Abstract only.
Kramer, L.D., and Vanderberg, J.P., "Intramuscular Immunization of Mice With Irradiated *Plasmodium Berghei* Sporozoites," *The American Journal of Tropical Medicine and Hygiene* 24(6):913-916, The American Society of Tropical Medicine and Hygiene, United States (1975).
Krzych, U., et al., "T Lymphocytes from Volunteers Immunized with Irradiated *Plasmodium falciparum* Sporozoites Recognize Liver and Blood Stage Malaria Antigens," *J. Immunol.* 155:4072-4077, American Association of Immunologists, United States (1995).
Labaied et al., "*Plasmodium yoelii* Sporozoites with Simultaneous Deletion of P52 and P36 are Completely Attenuated and Confer Sterile Immunity against Infection," *Infect Immun.* Aug. 2007;75(8):3758-3768, American Society for Microbiology, United States (2007).
Long, C.A., and Hoffman, S.L., "Malaria—from Infants to Genomics to Vaccines," *Science* 297:345-347, American Association for the Advancement of Science, United States (Jul. 2002).
Luke, T.C., and Hoffman, S.L., "Rationale and plans for developing a non-replicating, metabolically active, radiation-attenuated *Plas*-

(56) References Cited

OTHER PUBLICATIONS modium falciparum sporozoite vaccine," *The Journal of Experimental Biology* 206:3803-3808, The Company of Biologists Ltd, England (2003).

Mattig, F.R., et al., "A simple method for the purification of *Eimeria tenella* sporozoites," *Appl. Parasitol.* 34:139-142, Gustav Fischer Verlag Jena, Germany (1993).

Ménard, R., "Knockout malaria vaccine?" *Nature* 433:113-114, Nature Publishing Group, England (2005).

Mueller, A-K. et al., "Genetically modified *Plasmodium* parasites as a protective experimental malaria vaccine," *Nature* 433:164-167, Nature Publishing Group, England (2005).

Mueller, A-K et al., "Plasmodium liver stage developmental arrest by depletion of a protein at the parasite-host interface," *Proc Natl Acad Sci U S A.* 102(8):3022-3027, The National Academy of Sciences, United States (2005).

Nussenzweig, R.S. et al., "Protective Immunity produced by the Injection of X-irradiated Sporozoites of *Plasmodium berghei,*" *Nature* 216:160-162, Nature Publishing Group, England (1967).

Nussenzweig, R., "Use of Radiation-attenuated Sporozoites in the Immunoprophylaxis of Malaria," *International Journal of Nuclear Medicine and Biology* 7:89-96, Pergamon Press Ltd, England (1980).

Ockenhouse, C.F., et al., "Phase I/IIa Safety, Immunogenicity, and Efficacy Trial of NYVAC-Pf7, a Pox-Vectored, Multiantigen, Multistage Vaccine Candidate for *Plasmodium falciparum* Malaria," *The Journal of Infectious Diseases* 177:1664-1673, The University of Chicago, United States (1998).

Plowe, C.V., et al., "The Potential role of vaccines in the elimination of falciparum malaria and the eventual eradication of malaria," *J. Infect. Dis.* 200:1646-1649, Oxford University Press, United Slates (Dec. 2009).

Pombo, D.J., et al., "Immunity to malaria after administration of ultra-low doses of red cells infected with *Plasmodium falciparum,*" *The Lancet* 360(9333):610-617, Lancet Publishing Group, England (2002).

Purcell et al., "Chemical attenuation of Plasmodium berghei sporozoites induces sterile immunity in mice," *Infect. Immun.* 76:1193-1199, American Society for Microbiology, United States (2008).

Purcell et al., "Chemically attenuated *Plasmodium* sporozoites induce specific immune responses, sterile immunity, and cross-protection against heterologous challenge," *Vaccine* 26(38): 4880-4884, National Institutes of Health, United States (2008).

Rénia, L. et al, "Vaccination against malaria with live parasites," *Expert Rev. Vaccines* 5:473-481, Future Drugs Ltd, United Kingdom (2006).

Rénia L., "Protective immunity against malaria liver stage after vaccination with live parasites," *Parasite* 15(3):379-83 (2008).

Richie, T.L., and Saul, A., "Progress and challenges for malaria vaccines," *Nature* 415:694-701, Macmillan Magazines Ltd, England (2002).

Rieckmann, K.H., "Human immunization with attenuated sporozoites," *Bulletin of the World Health Organization* 68 (Suppl):13-16, World Health Organization, Switzerland (1990).

Roestenberg, M.D., "Protection against Malaria Challenge by Sporozoite Inoculation," *New England Journal of Medicine* 361(5):468-476, Massachusetts Medical Society, United States (Jul. 2009).

Sedegah et al.," Cross-protection between attenuated *Plasmodium berghei* and *P. yoelii* sporozoites," *Parasite Immunology* 29:559-565, Blackwell Publishing Ltd, United States (2007).

Spitalny, G.L., and Nussenzweig, R.S., "Effect of Various Routes of Immunization and Methods of Parasite Attenuation on the Development of Protection Against Sporozoite-Induced Rodent Malaria," *Proceedings of the Helminthological Society* 39 (Special Issue):506-514, United States (1972).

Trager,W. and Jenen, J.B., "Continuous Culture of *Plasmodium Falciparum*: its Impact on Malaria Research," *International Journal for Parasitology* 27(9):989-1006, Elsevier Science Ltd., Great Britain (1997).

Vanbuskirk et al., "Preerythrocytic, live-attenuated *Plasmodium falciparum* vaccine candidates by design," *Proc Natl Acad Sci U S A.* 106(31):13004-13009, The National Academy of Sciences, United States (Aug. 2009).

Van Dijk et al., "Genetically attenuated, P36p-deficient malarial sporozoites induce protective immunity and apoptosis of infected liver cells," *Proc Nail Acad Sci U S A.* 102(34):12194-12199, The National Academy of Sciences, United States (2005).

Van Schaijk et al., "Gene disruption of *Plasmodium falciparum* p52 results in attenuation of malaria liver stage development in cultured primary human hepatocytes," *PLoS One* 3(10):e3549 (2008).

Warburg, A. and Miller, L.H., "Sporogonic Development of a Malaria Parasite in Vitro," *Science* 255(5043):448-450, American Association for the Advancement of Science, United States (1992).

Warburg, A. et al., "In vitro culture of the mosquito stage of *Plasmodium falciparum,*" *Experimental Parasitology* 76(2):121-126, Academic Press, Inc, United States (1993).

Waters, A.P., et al., "Malaria Vaccines: Back to the Future?," *Science* 307:528-530, AAAS, United States (2005).

Wood, D.E., et al., "The Use of Membrane Screen Filters in the Isolation of *Plasmodium berghei* Sporozoites from Mosquitos," *Bulletin of the World Health Organization* 57(Suppl. 1):69-74 (1979).

Wykes, M. and Good M.F., "A case for whole-parasite malaria vaccines,"*Int. J. Parasitol.* 37:705-712, Academic Press, Inc., United States (2007).

The International Search Report and Written Opinion of the International Searching Authority issued in Int'l Patent Application No. PCT/US2010/20564, 12 pages, mailed Mar. 9, 2010.

Supplementary European Search Report and Opinion for EP Appl. No. 10731974.1, Munich, Germany, mailed on Aug. 14, 2012.

Arevalo-Herrera, M. et al., *Plasmodium vivax* malaria vaccine development.: Molecular Immunology 38(6)443-455, Elsevier Science Ltd. (2001).

Bojang, KA et al., "Efficacy of RTS,S/AS02 malaria vaccine against *Plasmodium falciparum* infection in semi-immune adult men in The Gambia: a randomized trial," *Lancet* 358(9297):1927-34 (2001).

Clyde, DF et al., "Specificity of Protection of Man Immunized Against Sporozoite-Induced Falciparum Malaria," *Am. J. Med. Sci.* 266:398-401 (1973).

Clyde, D.F., et al., "Immunization of Man Against Sporozoite-Induced Falciparum Malaria," *Am. J. Med. Sci.* 266:169-177 (1973).

Collins, W.E., et al., "Adaptation of a strain of *Plasmodium vivax* from Mauritania to New World monkeys and Anopheline Mosquitoes," *J. Parasitol.* 84:619-621, American Society of Parasitologists (Jun. 1998).

Collins, W.E., et al., "Potential of the Panama strain of Plasmodium vivax for the testing of malarial vaccines in *Aotus nancymai* monkeys," Am. J. Trop. Med. Hyg. 67:454-458, American Society for Tropical Medicine and Hygiene (Nov. 2002).

Egan JE, et al., "Humoral immune responses in volunteers immunized with irradiated *Plasmodium falciparum* sporozoites," *J Trop Med and Hygiene* 49:166-173(1993).

Food and Drug Administration, "Guidance for Industry, Content and Format of Chemistry, Manufacturing and Controls Information and Establishment Description Information for a Vaccine or Related Product," http://www.fda.gov/cber/guidelines.htm, (1999).

Garfield, R.M. & Vermund, S.H., "Changes in Malaria Incidence After Mass Drug Administration in Nicaragua," *The Lancet* 322: 500-503, Elsevier, UK (1983).

Gerberg, E.J., "Manual for Mosquito Rearing and Experimental Techniques", American Mosquito Control Association, Inc., Bulletin No. 5 (Jan. 1979).

Grady et al., "Program and Abstracts of the 40$^{st}$ Annual Meeting of the American Society of Tropical Medicine and Hygiene," Supplement to *The American Journal of Tropical Medicine and Hygiene* 47 (4): 218 (1992), Abstract only.

(56) References Cited

OTHER PUBLICATIONS

Hamilton D.R., et al., "An Integrated System for Production of Gnotobiotic Anopheles quadrimaculatus," Journal of Invertebrate Pathology 30:318-324, Academic Press, New York and London (1977).
Hurd, H. et al., "In vitro methods for culturing vertebrate and mosquito stages of Plasmodium," *Microbes and Infection* 5:321-327, Editions scientifiques et medicales Elsevier SAS, France (2003).
Hurtado et al. "Regular production of infective sporozoites of *Plasmodium falciparum* and *P. vivax* in laboratory-bred Anopheles albimanus," *Anals Trop. Med. & Parasit.* 91:49-60 (1997).
Li, X., et al., "Design of poten CD1d-binding NKT cell ligand as a vaccine adjuvant," *PNAS* 107 (29): 13010-13015 (2010).
Lin, K., et al., "In Vivo Protection Provided by a Synthetic New Alpha-Galactosyl Ceramide Analog against Bacterial and Viral Infections in Murine Models," *Antimicrobial Agents and Chemotherapy* 54(10), 4129-4136, American Society for Microbiology, United States (2010).
Malik, A., et al., "Human cytotoxic T lymphocytes against the Plasmodium falciparum circumsporozoite protein." Proc. Natl. Acad. Sci. 88: 3300-3304, National Academy of the Sciences, United States (1991).
Miller, L. et al., "Research toward vaccines against malaria," Nature Medicine Vaccine Supplement, 4:5, 520-524, Nature America Inc., United States (1998).
Munderloh U.G, et al., "*Anopheles stephensi* and *Toxorhynchites amboinensis*: aseptic rearing of mosquito larvae on cultured cells," *J. Parasit.* 68, 1085-91 (1982).
Munderloh U.G, et al., "Malarial Parasites Complete Sporogony in Axenic Mosquitoes," *Experientia* 41:1205-1207, Birkhauser Verlag AG (Sep. 1985).
Okiro, E.A., et al., "The decline in paediatric malaria admissions on the coast of Kenya," *Malaria Journal* 6:151:1-11, BioMed Central, Uk (2007).
Padte, N., et al., "Clinical development of novel CD1d-binding NKT cell ligand as a vaccine adjuvant," *Clinical Immunology* 140: 142-151, Elsevier Ltd., United States (2011).
Rieckmann, K., et al, "Sporozoite Induced Immunity in Man Against an Ethiopian Strain of *Plasmodium falciparum*," *Royal Society of Tropical Medicine and Hygiene* 68:258-259 (1974).
Kester, KE et al., "Efficacy of recombinant circumsporozoite protein vaccine regimens against experimental *Pasmodium falciparum* malaria," *J. Infect. Dis.* 183:640-7 (2001).
Rosales-Ronquillo, M.C. et al., "Aspetic Rearing of Anopheles stephensi," Annals of the Entomological Society of America. 66:949-954 , Entomological Society of America (Sep. 1973).
Schofield, L., et al., "Synthetic GPI as a candidate anti-toxic vaccine in a model of malaria," Nature 418:785-789, Nature Publishing Group (Aug. 2002).
Schuster, F. "Cultivation of *Plasmodium* spp.," Clinical Microbiology Reviews 15:3, 355-364, American Society for Microbiology, United States (2002).
Smith, D.L., et al., "Revisiting the Basic Reproductive Number for Malaria and Its Implications for Malaria Control," PLoS Biology 5:0531-0542, www.plosbiology.org, United States (2007).
Stoute, JA, et al. Long-term efficacy and immune responses following immunization with the RTS, S malaria vaccine. J. Infect. Dis. 178:1139-44 (1998).
Tsuji, M. et al., "Progress toward a Malaria Vaccine: Efficient Induction of Protective Anti-Malaria Immunity," Biol. Chem. 382(4):553-570, Walter de Gruyter, Berlin and New York (2001).
Vanderberg, J.P., "Development of Infectivity by the Plasmodium berghei Sporozoite," The Journal of Parasitology 61(1):43-50, The American Society of Parasitologists (1975).
Wu, Y., et al., "Phase 1 Trial of Malaria Transmission Blocking Vaccine Candidates Pfs25 and Pvs25 Formulated with Montanide ISA 51," PLoS Biology 3: 1-9, www.plosbiology.org, United States (2008).

Zapata, J.C., et al., "Reproducible infection of intact *Aotus lemurinus griseimembra* monkeys by Plasmodium falciparum sporozoite inoculation," J. Paristol. 88:723-729, American Society of Parasitologists (Aug. 2002).
Esp@cenet Database, English language abstract of CN1142887A, published Dec. 18, 1995 (listed as document FP6 on the accompanying form PTO/SB/08A).
Esp@cenet Database, English language abstract of CN1213497A, published Oct. 8, 1997 (listed as document FP7 on the accompanying form PTO/SB/08A).
Brossay, L., et al., "Mouse CD1 is mainly expressed on hemopoietic-derived cells," *J. Immunol.* 159:1216-1224, Williams & Wilkins, United States (1997).
Brossay, L., el al., "CD1d-mediated Recognition of an α-Galactosylceramide by Natural Killer T Cells is Highly Conserved though Mammalian Evolution," *J. Exp. Med.* 188(8):1521-1528, Rockefeller University Press, United States (1998).
Epstein, J. E., et al. "Live Attenuated Malaria Vaccine Designed to Protect Through Hepatic CD8+ T Cell Immunity," *Science* 334 (6055):475-480, American Association for the Advancement of Science, United States (2011).
Fujii, S., et al., "Activation of natural killer T cells by alpha-galactosylceramide rapidly induces the full maturation of dendritic cells in vivo and thereby acts as an adjuvant for combined CD4 and CD8 T cell immunity to a coadministered protein," *J. Exp. Med.* 198:267-279, Rockefeller University Press, United States (2003).
Fujii, S., et al., "The linkage of innate adaptive immunity via maturing dendritic cells in vivo requires CD40 ligation in addition to antigen presentation and CD80/86 costimulation,"*J. Exp. Med.* 199:1607-18, Rockefeller University Press, United States (2004).
Giaccone, G., et al., "A phase I study of the natural killer T-cell ligand alpha-galactosylceramide (KRN7000) in patients with solid tumors," *Clin. Cancer Res.* 8:3702-3709, The Association, United States (2002).
Gonzalez-Aseguinolaza, G., et al., "Natural killer T Cell ligand alpha-galactosylceramide enhances protective immunity induced by malaria vaccines," *J. Exp. Med.* 195:617-624, Rockefeller University Press, United States (2002).
Hermans, I.F., et al., "NKT cells enhance CD4+ and CD8+ T cells responses to soluble antigen in vivo through direct interaction with dendritic cells," *J. Immunol.* 171:5140-5147, American Association of Immunologists, United States (2003).
Huang, Y., et al., "Enhancement of HIV DNA vaccine immunogenicity by the NKT cell ligand, alpha-glactosylceramide," *Vaccine* 26:1807-1816, Elsevier Science, Netherlands (2008).
Kawano, T., et al., "CD1d-restricted and TCR-mediated activation of vaplhal4 NKT cells by glycosylceramides," *Science* 278(5343):1626-1629, American Association for the Advancement of Science, United States (1997).
Ishikawa, A., et al., "A phase I study of alpha-galactosylceramide (KRN7000)-pulsed dendritic cells in patients with advanced and recurrent non-small cell lung cancer," *Clin. Cancer Res.* 11(5):1910-1917, The Association, United States (2005).
Ko, S.Y., et al., "alpha-Galactosylceramide can act as a nasal vaccine adjuvant inducing protective immune responses against viral infection and tumor," *J. Immunol.* 175:3309-3317, American Association of Immunologists, United States (2005).
Koboyashi, E., et al., "KRN7000, a novel immunomodulator, and its antitumor activities," *Oncol. Res.* 7(10-11): 529-534, Cognizant Communication, United States (1995).
Mandal, M., et al.; "Tissue distribution regulation and intracellular localization of murine CD1 molecules,"*Mol. Immunol.* 35:525-536, Pergamon Press, England (1998).
Nieda, M., et al., "Therapeutic activation of Valpha24+Vbeta11+ NKT cells in human subjects results in highly coordinated secondary activation of acquired and innate immunity," *Blood* 103(2):383-389, American Society of Hematology, United States.
Roark, J.H., et al., "CD1.1 expression by mouse antigen-presenting cells and marginal zone B cells," *J. Immunol.* 160:3121-3127, American Association of Immunologists, United States (1998).
Seino, K., et al., "Natural killer T cell-mediated antitumor immune responses and their clinical applications," *Cancer Sci* 97:807-812, Blackwell Publishing, England (2006).

(56) References Cited

OTHER PUBLICATIONS

Tomura, M., et al., "A novel function of Valpha14+CD4+NKT cells: stimulation of IL-12 production by antigen-presenting cells in the innate immune system, "*J. Immunol.* 163:93-101, American Association of Immunologists, United States (1999).

Vaughan, A.M. et al., "Vaccination using radiation- or genetically attenuated live sporozoites," *Methods in Molecular Biology* 923:549-566 (2013).

Co-pending U.S. Appl. No. 15/095,360 (inventors Eappen el al.), filed Apr. 11, 2016 (Not Published).

Co-pending U.S. Appl. No. 15/060,959 (inventors Felgner et al.), filed Mar. 4, 2016 (Not Published).

Office Action mailed Jun. 28, 2016 in U.S. Appl. No. 15/002,443, Sim, et al., filed Jan. 21, 2016.

Office Action mailed Sep. 13, 2010, in U.S. Appl. No. 12/684,863, Sim, B.K.L., et al., filed Jan. 8, 2010.

Office Action mailed Apr. 19, 2011, in U.S. Appl. No. 12/684,863, Sim, B.K.L., et al., filed Jan. 8, 2010.

Office Action mailed Feb. 6, 2012, in U.S. Appl. No. 12/870,102, Sim, B.K.L., et al., filed Aug. 27, 2010.

Office Action mailed Nov. 6, 2013, in U.S. Appl. No. 13/730,294, Graser, Jennifer E.., et al., filed Dec. 28, 2012.

Office Action mailed Apr. 29, 2013, in U.S. Appl. No. 13/470,128, Chakravarty, et al., filed May 11, 2012.

Office Action mailed Jul. 14, 2014, in U.S. Appl. No. 13/730,281, Sim, et al., filed Dec. 28, 2012.

Office Action mailed May 29, 2008, in U.S. Appl. No. 11/726,622, Hoffman, et al., filed Mar. 21, 2007.

Office Action mailed May 1, 2009, in U.S. Appl. No. 11/726,622, Hoffman, et al., filed Mar. 21, 2007.

Office Action mailed Nov. 13, 2009, in U.S. Appl. No. 11/726,622, Hoffman, et al., filed Mar. 21, 2007.

Office Action mailed Oct. 14, 2010, in U.S. Appl. No. 11/726,622, Hoffman, et al., filed Mar. 21, 2007.

Office Action mailed Aug. 21, 2013, in U.S. Appl. No. 11/726,622, Hoffman, et al., filed Mar. 21, 2007.

Office Action mailed Sep. 15, 2006, in U.S. Appl. No. 10/958,163, Hoffman, et al., filed Oct. 4, 2004.

PHARMACEUTICAL COMPOSITIONS COMPRISING ATTENUATED *PLASMODIUM* SPOROZOITES AND GLYCOLIPID ADJUVANTS

CROSS REFERENCE TO RELATED APPLICATIONS

This application is a divisional of U.S. application Ser. No. 14/065,012, filed Oct. 28, 2013, currently allowed, which is a continuation of U.S. application Ser. No. 13/470,128, filed May 11, 2012, now abandoned, which claims priority from U.S. Provisional Application No. 61/485,092, filed May 11, 2011, the contents of which are hereby incorporated by reference in their entireties.

FIELD OF THE INVENTION

The invention disclosed herein relates generally to pharmaceutical compositions comprising *Plasmodium* parasites useful as immunogens in vaccines for preventing or reducing the risk of malaria. More particularly, the invention relates to pharmaceutical compositions comprising *Plasmodium* sporozoite-stage parasites and glycolipid adjuvants wherein the compositions are useful for eliciting an immune response, conferring protective immunity in a host so as to prevent malaria, and reducing the incidence of malaria in hosts subsequently challenged with pathogenic *Plasmodium*, more particularly in mammalian or human hosts, and the invention relates to vaccines and methods of using the provided pharmaceutical compositions in vaccines for the prevention of malaria.

BACKGROUND OF THE INVENTION

There are >200 million malaria cases and ~1 million deaths per year caused by *Plasmodium falciparum* (Pf) (World Health Organization. Global Malaria Programme. World Malaria Report 2010: World Health Organization, 2010; Murray C J, et al. *Global malaria mortality between 1980 and 2010: a systematic analysis.* 2012 Lancet 379: 413-431). Recently, progress has been made controlling malaria due to investment of billions of dollars in the use of bednets, insecticides, and drugs. However, as highlighted in a recent editorial (Editorial: *Malaria* 2010: *More Ambition and Accountability Please* 2010 Lancet 375:1407), a commercially available malaria vaccine is still badly needed. To prevent infection, disease, and transmission an ideal single stage vaccine should target the pre-erythrocytic (sporozoite and liver) stages (Plowe C. V. et al. *The potential role of vaccines in the elimination of falciparum malaria and the eventual eradication of malaria* 2009 J. Infect. Dis. 200: 1646-1649; Alonso P. L. et al. *A research agenda for malaria eradication: vaccines.* 2011 PLoS Med 8: e1000398). Such a vaccine would have huge public- and private-sector markets. In public-sector markets it would be used in infants, young children, and adolescent females (preventing malaria during pregnancy) and for entire populations for geographically focused malaria elimination campaigns (Id.). Individuals from non-malarious countries who spend time in areas with malaria (travelers, military, government officials, students, business people, etc.) and middle and upper class residents of countries with malaria comprise the private-sector market.

Data indicating a highly effective vaccine might be possible came from trials in which volunteers immunized by the bites of mosquitoes infected with radiation-attenuated Pf sporozoites had high-level (>90%), sustained (≥10 months) protection against experimental challenge (Hoffman, S. L., et al. 2002 J. Inf. Dis. 185:1155-64).

It has been shown that a vaccine incorporating live attenuated Pf sporozoites can be manufactured (SANARIA™ PfSPZ Vaccine). This process has recently been described (Hoffman S. L. et al. *Development of a metabolically active, non-replicating sporozoite vaccine to prevent Plasmodium falciparum malaria.* 2010 Hum. Vac. 6:97-106. DOI: 10396 [pii].). The ability of PfSPZ Vaccine to induce antigen-specific immune responses in humans was also demonstrated (Epstein, J. E., et al. *Live Attenuated Malaria Vaccine Designed to Protect Through Hepatic $CD8^+$ T Cell Immunity* 2011 Science 334 (6055):475-480).

It is thought that an attenuated PfSPZ vaccine delivered by a parenteral non-intravenous route and capable of demonstrating a protective efficacy comparable to that achieved with PfSPZ administered IV would require large numbers of sporozoites and a multi-dose regimen. In a mouse model, present data suggests that approximately 7 times as many *Plasmodium yoelii* (Py) sporozoites administered intradermal (ID) or subcutaneous (SC) are required compared to IV administration in order to achieve >80% protection in mice (Epstein, et al., Id.). A more promising approach for the development of a highly effective parenteral non-IV vaccine would likely include the use of an adjuvant.

The adjuvant: A glycolipid adjuvant that stimulates natural killer T-cells (NKT) was identified in mice. (Gonzalez-Aseguinolaza G, et al. *Natural killer T cell ligand α-galactosylceramide enhances protective immunity induced by malaria vaccines* 2002 J. Exp. Med. 195: 617-624; U.S. Pat. No. 7,534,434). Using a single IV-administered dose of radiation attenuated *P. yoelii* sporozoites (suboptimal for protection) it was demonstrated in the Gonzalez-Aseguiniola paper that distal intraperitoneal (IP) administration of α-galactosylceramide (α-GalCer), a ligand for natural killer T (NKT) cells, could induce a higher degree of protection (>90%), than IV administration of irradiated *P. yoelii* sporozoites alone, which conferred only 20% protection.

Natural Killer T (NKT) cells are a subset of T cells that co-express receptors of T cell and NK cell lineages and recognize their cognate antigen presented by the MHC-like CD1d on antigen presenting cells (APCs). The major subset of NKT cells are distinguished by their restricted expression of an invariant TCR (invTCR) and are termed iNKT cells. The increased potency of IV administered sporozoites and distally administered IP adjuvant described in Gonzalez-Aseguinolaza et al. correlated with enhanced IFN-gamma secretion by $CD8^+$ T cells and was dependent on iNKT cells and CD1d (Id.). This first-identified iNKT TCR ligand, α-GalCer, extracted from the *Agelas mauritianus* sea sponge, was discovered while screening for compounds with anti-tumor activity. It has a high affinity for CD1d, is a potent activator of iNKT cells in both mouse and human, and has been used extensively to study the function of iNKT cells (Brossay L, et al. *CD1d-Mediated Recognition of an A-Galactosylceramide by Natural Killer T Cells is Highly Conserved through Mammalian Evolution* 1998 J. Exp. Med. 188:1521-1528; Kobayashi E, et al. *KRN7000, A Novel Immunomodulator, and its Antitumor Activities* 1995 Oncol. Res. 7: 529-534; Kawano T, et al., *CD1d-restricted and TCR-mediated activation of vα14 NKT cells by glycosylceramides* 1997 Science 278: 1626-1629. In vivo administration of α-GalCer in mice results in a cascade of events beginning with signaling through the invTCR by APCs expressing CD1d. Macrophages, dendritic cells, B cells, Kupffer cells in the liver, and hepatocytes all have constitutive expression of CD1d (Mandal M, et al., *Tissue distribution, regulation and intracellular localization of murine CD1 molecules* 1998 Mol. Immunol. 35: 525-536; Brossay L., et al., *Mouse CD1 is mainly expressed on hemopoietic-derived cells* 1997 J. Immunol 159: 1216-1224; Roark, J. H., et al., *A. CD1.1 expression by mouse antigen-presenting cells and marginal zone B cells* 1998 J. Immunol. 160: 3121-3127).

Stimulated iNKT cells rapidly secrete pre-stored cytokines (unlike traditional T cells) that reciprocally activate APCs (Tomura M., et al., *A novel function of Vα14+CD4+ NKT cells: stimulation of IL-12 production by antigen presenting cells in the innate immune system* 1999 J. Immunol. 163: 93-101; Fujii, S., et al., *Activation of natural killer T cells by α-galactosylceramide rapidly induces the full maturation of dendritic cells in vivo and thereby acts as an adjuvant for combined CD4 and CD8 T cell immunity to a coadministered protein* 2003 J. Exp. Med. 198: 267-279) enhancing their ability to prime $CD4^+$ and $CD8^+$ T cells (Fujii, S., et al., *The linkage of innate to adaptive immunity via maturing dendritic cells in vivo requires CD40 ligation in addition to antigen presentation and CD80/86 costimulation* 2004 J. Exp. Med. 199: 1607-1618; Hermans, I. F., et al., *NKT cells enhance CD4+ and CD8+ T cell responses to soluble antigen in vivo through direct interaction with dendritic cells* 2003 J. Immunol. 171: 5140-5147) to generate a powerful cell-mediated immune response. In the paper of Gonzales-Aseguinolaza et al., *supra*, the legend of FIG. 2A states that a group of BALB/c mice was immunized subcutaneously with irradiated sporozoites [*P. yoelii*] together with or without administration of α-GalCer by the same route, and when splenic lymphocytes were isolated and the number of IFN-γ-secreting CS-specific $CD8^+$ and $CD4^+$ T-cells were determined by ELISPOT assay it was found that co-administration of α-GalCer increased the number of IFN-γ-secreting CS-specific $CD8^+$ cells seven fold. Thus, the overall amplification of the adaptive immune response by iNKT cells made them very attractive adjuvant targets.

Subsequently, α-GalCer has been demonstrated to have adjuvant properties for influenza, HIV, and tumor vaccines in mice (Huang, Y., et al., *Enhancement of HIV DNA vaccine immunogenicity by the NKT cell ligand, α-galactosylceramide* 2008 Vaccine 26:1807-1816; Ko, S. Y., et al., *α-Galactosylceramide can act as a nasal vaccine adjuvant inducing protective immune responses against viral infection and tumor* 2005 J. Immunol. 175: 3309-3317; Seino, K., et al., *Natural killer T cell-mediated antitumor immune responses and their clinical applications* 2006 Cancer Sci. 97: 807-812).

Furthermore, because α-GalCer was discovered while screening for compounds with anti-tumor properties, it has been used in several clinical trials in cancer patients. Delivery by pre-loading autologous PBMCs with α-GalCer in vitro or by direct injection, α-GalCer was shown to be safe and well tolerated. However, although modest enhancement of immune responses was generally seen, its beneficial effects were limited (Giaccone, G., et al., *A phase I study of the natural killer T-cell ligand α-galactosylceramide (KRN7000) in patients with solid tumors* 2002 Clin. Cancer Res. 8:3702-3709; Ishikawa, A., et al., *A phase I study of α-galactosylceramide (KRN7000)-pulsed dendritic cells in patients with advanced and recurrent non-small cell lung cancer* 2005 Clin. Cancer Res. 11: 1910-1917; Nieda, M., et al., *Therapeutic activation of Vα24+Vbeta11+ NKT cells in human subjects results in highly coordinated secondary activation of acquired and innate immunity* 2004 Blood 103: 383-389).

Consequently, Tsuji and colleagues made an effort to find analogues of α-GalCer with increased CD1d-binding and iNKT-stimulatory properties. The particular advantages of identifying a new glycolipid adjuvant similar to α-GalCer and based on a CD1d-binding, iNKT-stimulatory effect are multi-fold. First, the phenotype and functional properties of the CD1d molecules and invTCR of iNKT cells have been conserved between humans and mice, thereby allowing prediction of the activity of related glycolipids in humans through mouse studies. Second, α-GalCer itself has been approved and well characterized in terms of safety and activity in humans. Third, related glycolipids used as vaccine adjuvant could be administered in much smaller quantities using a local parenteral route of administration (e.g. intramuscular) than the larger doses of α-GalCer currently dispensed IV for cancer therapy, thereby further minimizing potential systemic side effects.

Tsuji and colleagues screened a library of synthetic α-GalCer analogues and identified glycolipids with far greater CD1d binding and activation of iNKT cells (Li, X., et al., *Design of a potent CD1d-binding NKT cell ligand as a vaccine adjuvant* 2010 Proc Natl Acad Sci USA 107: 13010-13015; U.S. Pat. No. 7,923,013). One such glycolipid, was 7DW8-5 (FIG. 1). Structurally, 7DW8-5 possesses a fluorinated benzene ring at the end of C10 length fatty acyl chain. It was selected due to its superior ability to elicit cytokine production from human and mouse iNKT cells and its adjuvant properties in mice when used in combination with a suboptimal dose of a recombinant adenovirus expressing *P. yoelii* CS protein. The adjuvant was co-administered intramuscularly (IM) with the vaccine. The mice were challenged with pathogenic *P. yoelii* sporozoites 2 weeks later. 7DW8-5 enhanced the malaria-specific $CD8^+$ T cell response significantly more than α-GalCer and also enhanced the malaria-specific humoral response equally if not slightly stronger than α-GalCer. Finally, 7DW8-5 was able to display a significantly stronger adjuvant effect than α-GalCer in enhancing protective efficacy of the adenovirus recombinant vaccine after a single immunizing dose.

The practical considerations for the preclinical and clinical development of 7DW8-5 as an adjuvant for candidate recombinant subunit malaria vaccines was recently discussed (Padte, N. N., et al., *Clinical development of a novel CD1d-binding NKT cell ligand as a vaccine adjuvant* 2010 Clin. Immunol. doi: 10.1016/j.clim.2010.11.009).

There is a need for improved malaria vaccines. With regard to malaria vaccines whose immunogen is live attenuated *Plasmodium* parasites, particularly sporozoite-stage parasites, an adjuvant that could reduce the numbers of doses and the dosages of each dose required for highly effective protection would have enormous value in the fight against malaria. For instance, a vaccine administered in 1 or 2 doses would not only reduce the cost of goods to produce it, but more importantly it would simplify the logistics of delivery for travelers, for rapidly deployed military, or for mass-immunization campaigns.

SUMMARY OF THE INVENTION

Disclosed herein are pharmaceutical compositions comprising one or more species of live, *Plasmodium* sporozoite-stage parasites, a glycolipid adjuvant, and an excipient.

Also disclosed are methods of using these pharmaceutical compositions for reducing the risk of malaria in an individual and reducing the incidence of malaria among a group of individuals exposed to pathogenic *Plasmodium* parasites. These methods comprise administration of 1 or more doses of the pharmaceutical compositions provided herein prior to said exposure.

Also disclosed are improved malaria vaccines whose immunogen comprises either live attenuated *Plasmodium* sporozoites, or live non-attenuated sporozoites delivered along with the protection of an anti-malarial drug such as chloroquine, each of which being useful for the prevention of malaria. Compositions of live *Plasmodium* sporozoites and the glycolipid adjuvants disclosed herein are compatible in pharmaceutical compositions and surprisingly effective in reducing the number of doses and/or reducing the effective sporozoites dosage.

DETAILED DESCRIPTION OF THE INVENTION

Definitions

Figures 1A, 1B:
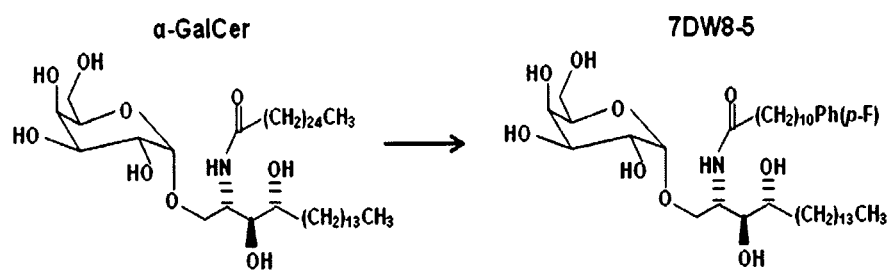
FIGS. 1A and 1B—Depict the structures of α-GalCer and 7DW8-5, respectively.

The terms "about" or "approximately" means within one standard deviation as per the practice in the art.

"Additive" as used herein as a noun is a compound or composition added to a sporozoite preparation to facilitate preservation of the preparation. Additives may include cryoprotectants such as DMSO and glycerol, antioxidants, and the like.

"Conferring protective immunity" as used herein refers to providing to a population, a group of individuals or a host (i.e., an individual), the ability to generate an immune response which in turn protects against, i.e. prevents, a disease, malaria in this case, caused by a pathogen (e.g. *Plasmodium falciparum*) such that the clinical manifestations, pathology, or symptoms of disease in a host exposed to the pathogen are reduced as compared to a non-treated host, or such that the rate at which infection, or clinical manifestations, pathology, or symptoms of disease appear within a population are reduced, as compared to a non-treated population, group or individual.

"Immune response" as used herein means a response in the recipient to the introduction of attenuated sporozoites generally characterized by, but not limited to, production of antibodies and/or T cells. Generally, an immune response may be a cellular response such as induction or activation of CD4+ T cells or CD8+ T cells specific for *Plasmodium* species epitopes, a humoral response of increased production of *Plasmodium*-specific antibodies, or both cellular and humoral responses. With regard to a malaria vaccine, the immune response established by a vaccine comprising sporozoites includes but is not limited to responses to proteins expressed by extracellular sporozoites or other stages of the parasite after the parasites have entered host cells, especially hepatocytes and mononuclear cells such as dendritic cells and/or to components of said parasites. In the instant invention, upon subsequent challenge by infectious organisms, the immune response prevents or exhibits development of pathogenic parasites to the asexual erythrocytic stage that causes disease.

"Intravenous" (abbreviated as IV) as defined herein means intentional introduction, directly into the lumen of an identified large blood vessel such as a vein.

"Metabolically active" as used herein means alive, and capable of performing sustentative functions and some lifecycle processes. With regard to attenuated sporozoites this includes sporozoites that are capable of invading hepatocytes in culture and in vivo, progressing through some developmental stages within hepatocytes, and displaying de novo expression of stage-specific proteins.

"Parenteral" as defined herein means not through the alimentary canal, but rather by introduction through some other route, as intradermal (ID), subcutaneous (SC), intramuscular (IM), intraperitoneal (IP), intravenous (IV), and the like.

"Pharmaceutical composition" as defined herein means a sterile composition comprising one or more active ingredients, produced aceptically, under cGMP protocol, such that the composition would be acceptable for use in human subjects.

"Therapeutic" as defined herein relates to reduction of clinical manifestations or pathology which have already become manifest. A "therapeutically effective amount" as used herein means an amount sufficient to reduce the clinical manifestations, pathology, or symptoms of disease in an individual, or an amount sufficient to decrease the rate at which clinical manifestations, pathology, or symptoms of disease appear within a population.

"Vaccine" as used herein is a preparation comprising an immunogenic agent and a pharmaceutically acceptable diluent in combination with excipient, adjuvant and/or additive or protectant. The immunogen may be comprised of a whole infectious agent or a molecular subset of the infectious agent (produced by the infectious agent, or produced synthetically or recombinantly). When the vaccine is administered to a subject, the immunogen stimulates an immune response such that, upon subsequent challenge with infectious agent, will protect the subject from illness or mitigate the pathology, symptoms or clinical manifestations caused by that agent. A therapeutic (treatment) vaccine is given after infection and is intended to reduce or arrest disease progression. A preventive (prophylactic) vaccine is intended to prevent initial infection or reduce the rate or burden of the infection. Agents used in vaccines against a parasitic disease such as malaria may be whole-killed (inactive) parasites, live-attenuated parasites (unable to fully progress through their life cycle), live, fully infectious parasites administered with an anti-malarial drug, or purified or artificially manufactured molecules associated with the parasite e.g. recombinant proteins, synthetic peptides, DNA plasmids, and recombinant viruses or bacteria expressing *Plasmodium* proteins. A vaccine may comprise sporozoites along with other components such as excipient, diluent, carrier, antimalarial drug, preservative, adjuvant or other immune enhancer, or combinations thereof, as would be readily understood by those in the art.

Chemical nomenclature as used herein is as follows: "R" represents a variable chemical structure attached at the indicated location in a family of compounds; "Me" represents a methyl group attached at the indicated location; "Ph" represents a phenolic ring attached at the indicated location; "(p-OMe)" or "(p-F)" or "(p-$CF_3$)" following Ph represents the corresponding moiety located at the para position of the phenolic ring; "F" represents a fluoride moiety located attached at the indicated location; "O" represents an oxygen moiety, "C" represents a carbon moiety; and "H" represents a hydrogen moiety.

Pharmaceutical Compositions Comprising *Plasmodium* Sporozoites

In addition to the live attenuated PfSPZ Vaccine described above, there is another approach to whole sporozoite malaria vaccine development called chemoprophylaxis with sporozoites (CPS), and requires the bite of only 45 mosquitoes (3 times 15 mosquitoes) carrying fully infectious PfSPZ of volunteers taking chloroquine chemoprophylaxis to achieve 95% sterile protective immunity (19/20 volunteers) and that lasts for at least 28 months (Roestenberg M, et al. *Protection Against a Malaria Challenge by Sporozoite Inoculation.* 2009 N. Eng. J. Med. 361: 468-477; Roestenberg M, et al. *Long-term Protection Against Malaria After Experimental Sporozoite Inoculation: an Open-label Follow-up Study.* 2011 Lancet 377: 1770-1776). This is 20-25 times fewer PfSPZ-infected mosquitoes than the 1,000 required for the irradiated PfSPZ approach (Hoffman S L, et al. *Protection of humans against malaria by immunization with radiation-attenuated Plasmodium falciparum sporozoites* 2002 J. Infect. Dis. 185:1155-1164). As disclosed in Roestenberg 2009, incorporated herein by reference, the antimalarial drug (e.g., chloroquine) is administered to the host prior to the first administration of *Plasmodium* immunogen in the vaccination regimen, usually at least 2 days prior to first dose, and administration of the antimalarial continues, usually for at least 30 days subsequent to the last dose in the regimen, such that the level of antimalarial in the bloodstream of said host is sufficient to prevent the signs, symptoms and pathology of malaria. For example, as disclosed in Roestenberg (*Id.*), chloroquine may be administered orally in two 300 mg doses starting 2 days prior to the first exposure to SPZ and continuing in weekly 300 mg doses until 1 month after the last exposure. It is a transformative approach to human vaccination because it harnesses the infectious agent's inherent replicative properties to amplify production of protective immunogens spanning multiple developmental stages, and then eliminates the infectious agent with an anti-infective drug before the onset of disease. For either vaccine, an adjuvant that increases the potency of the SPZ sporozoite would be of enormous value.

Most of the technical hurdles in the development of malaria vaccines comprising pharmaceutical compositions of live attenuated sporozoites and live infectious sporozoites have now been overcome—among them, aseptic production of sufficient quantities of sporozoites isolated from attendant material using cGMP protocol (See particularly U.S. Pat. No. 7,229,627; Hoffman, S L, et al., 2010 Hum. Vac. 6:97-106—both explicitly incorporated herein by reference).

Regarding a vaccine suitable for routine use in human subjects that comprises live attenuated sporozoites, and live infectious sporozoites, the sporozoites must be substantially purified from the source from which they were produced. Pharmaceutical compositions comprising substantially purified sporozoites and excipient as well as methods of purifying sporozoites are known in the art (U.S. Patent Publ. No. 2010/0183680. This publication is explicitly incorporated herein by reference.

*Plasmodium*-species parasites are grown aseptically in cultures as well as in vivo in *Anopheles*-species mosquito hosts, most typically *Anopheles stephensi* hosts. Methods of axenically culturing *Plasmodium*-species liver stage parasites (Kappe et al. US Pub. 2005/0233435) and methods of producing attenuated and non-attenuated *Plasmodium*-species sporozoites, particularly, methods of growing and attenuating parasites in mosquitoes, and harvesting attenuated and non-attenuated sporozoites are known in the art and have been described (See: U.S. Pat. No. 7,229,627; U.S. Pub. No. 2005/0220822).

PfSPZ Vaccine, a malaria vaccine comprising live attenuated *Plasmodium* sporozoites without adjuvant, has been developed and is in clinical trials (Hoffman S. L. et al., *Development of a metabolically active, non-replicating sporozoite vaccine to prevent Plasmodium falciparum malaria.* 2010 Hum. Vac. 6:97-106. DOI: 10396 [pii].). The vaccine has already been assessed in a first-in-humans Phase 1 clinical trial in 80 healthy, malaria-naive adults at Naval Medical Research Center and the University of Maryland (Epstein J. E., et al. *Supra.*). The vaccine was administered intradermally (ID) or subcutaneously (SC) to 80 volunteers with the primary goal of establishing safety. Results of this dose-escalation study demonstrated the PfSPZ Vaccine is safe, well tolerated, and without breakthrough infections. Furthermore, the vaccine induced antibody and T cell immune responses, and protected several volunteers. However, as expected based on pre-clinical data, optimal immune responses and protection were not achieved in this first trial and studies in mice, rabbits, and monkeys have pointed the way toward the next steps in the R&D process (Epstein, J. E. et al, *Id.*). The Pf sporozoites in the PfSPZ Vaccine are highly potent. Based on animal studies, it appears that the effectiveness of pre-erythrocytic stage malaria vaccines correlates with the induction of interferon gamma producing CD8+ T cells in the liver. It is expected that this immune response will eliminate the Pf-infected liver cells. When rhesus monkeys were immunized intravenously (IV) with the PfSPZ Vaccine, 4 months after the last dose, 3% of all CD8+ T cells in the liver were specific for PfSPZ. No such responses were seen in monkeys immunized by the SC route, as was done in the first clinical trial. In mice, IV administration of irradiated, purified, cryopreserved *P. yoelii* SPZ induced high levels of protection at low doses; 88% (21/24) of mice were fully protected after 3 doses of 2,000 irradiated PySPZ. When administered SC or ID, as in the first clinical trial, immune responses were 50 to 150 fold lower and it required 7 to 10 times as many sporozoites to achieve high level protection.

It is anticipated that IV administration of the vaccine will reduce the number of sporozoites required to provide protection against subsequent challenge with pathogenic parasites and effectively reduce the incidence of malaria among a group of individuals exposed to pathogenic *Plasmodium* parasites. However, even in mice, it currently requires 3 doses administered IV to achieve high level protection, and it would be preferable to achieve such protection with fewer doses. Furthermore, administration by a parenteral non-IV route would be preferable. Therefore, it is desirable to reduce the number of sporozoites per dose, and perhaps the number of doses, required to confer protective immunity by a parenteral non-IV route of administration. These requirements provide the framework for identifying an effective adjuvant that is compatible for use with live attenuated sporozoites.

Prior to the discovery disclosed herein, no adjuvant had been described as compatible with live attenuated *Plasmodium* sporozoites. The successful development of a sporozoite-compatible adjuvant to maximize the protective efficacy of parenterally administered sporozoites is universally applicable to sporozoites attenuated by all means, including radiation, chemicals or genetic alteration, thereby enabling a highly effective vaccine for the prevention of malaria delivered by a parenteral route (IV or non-IV).

Methods of Making Glycolipids

The methods of synthesis of the glycolipid analogues of the present invention are provided in Tsuji et al (U.S. Patent Publ. No. 2007/02388871, explicitly incorporated by reference). Unlike laboratory reagents for use in small animal studies, all biologic substances must be manufactured under Good Manufacturing Practice (GMP) conditions (Code of Federal Regulations Title 21, Part 211, April 2009) before use in humans One of the practical advantages of glycolipids is their straightforward synthesis pathway from chemical compounds that are readily available at relatively low cost. In order for glycolipids to function as effective adjuvants that provide dose-sparing of vaccines against infectious diseases with high prevalence in the developing world, low cost and ease of manufacturing are desirable (Padte, et al., at page 4).

Five analogues of α-GalCer were chosen based on enhanced stimulatory activity against human iNKT cells in vitro, binding affinity to human and murine CD1d molecules, and binding affinity to the invariant t cell receptor of human iNKT cells (Li, X., et al., *Design of a potent CD1d-binding NKT cell ligand as a vaccine adjuvant* 2010 Proc Natl Acad Sci USA 107: 13010-13015, explicitly incorporated herein by reference).

The genus of the 5 analogues is shown schematically in formula (1):

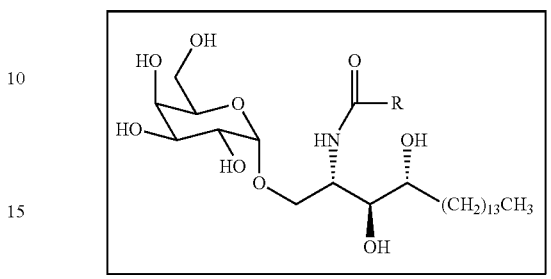

where R is: $(CH_2)_5Ph(p\text{-}OMe)$; $(CH_2)_7Ph(p\text{-}OMe)$; $(CH_2)_7Ph(p\text{-}F)$; $(CH_2)_{10}Ph(p\text{-}F)$; or $(CH_2)_{10}Ph(p\text{-}CF_3)$.

Each of these 5 analogues are designated as follows:

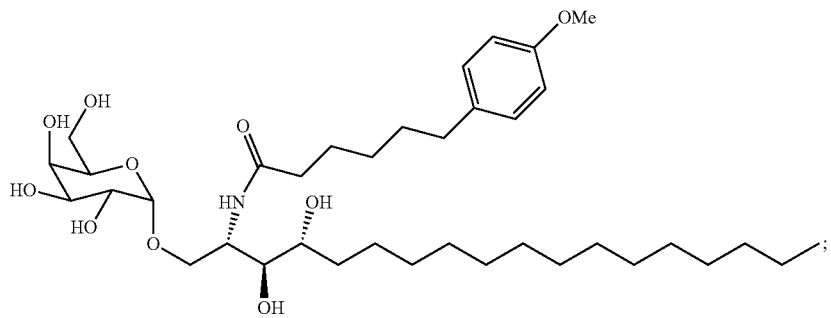 [SMILES: CCCCCCCCCCCCCC[C@@H](O)[C@@H](O)[C@H](COC1OC(CO)C(O)C(O)C1O)NC(=O)CCCCCc1ccc(OC)cc1]

formula (2) (designated as C18 in Li et al., and designated formula 101 in U.S. Pat. No. 7,923,013)

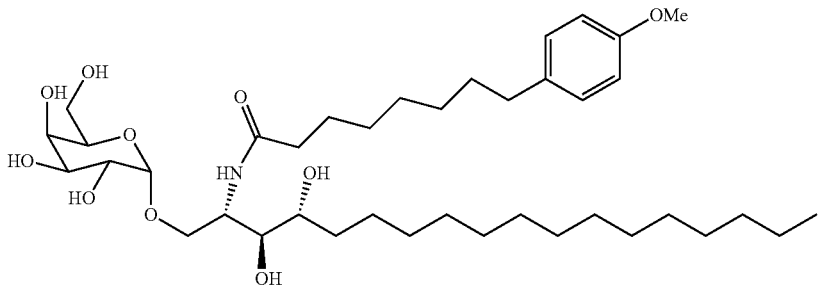 [SMILES: CCCCCCCCCCCCCC[C@@H](O)[C@@H](O)[C@H](COC1OC(CO)C(O)C(O)C1O)NC(=O)CCCCCCCc1ccc(OC)cc1]

formula (3) (designated as C22 in Li et al., and designated as formula 102 in U.S. Pat. No. 7,923,013)

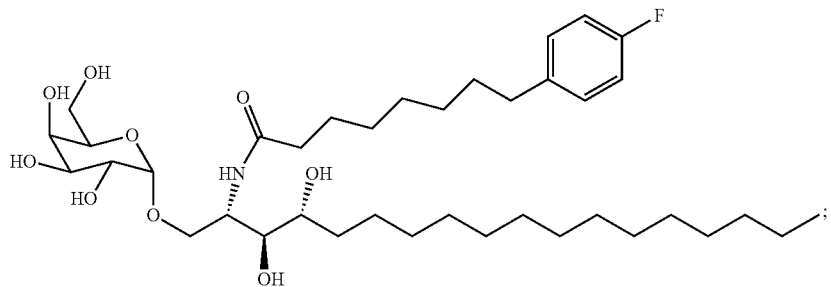 [SMILES: CCCCCCCCCCCCCC[C@@H](O)[C@@H](O)[C@H](COC1OC(CO)C(O)C(O)C1O)NC(=O)CCCCCCCc1ccc(F)cc1]

formula (4) (designated as C23 in Li et al., and designated as formula 104 in U.S. Pat. No. 7,923,013)

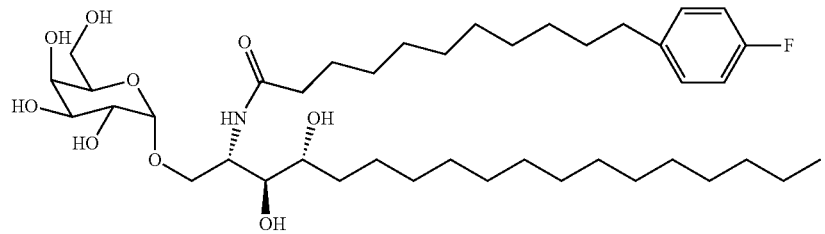 [SMILES: CCCCCCCCCCCCCC[C@@H](O)[C@@H](O)[C@H](COC1OC(CO)C(O)C(O)C1O)NC(=O)CCCCCCCCCCc1ccc(F)cc1]

formula (5) (designated as 7DW8-5 in Li et al., and designated as formula 105 in U.S. Pat. No. 7,923,013)

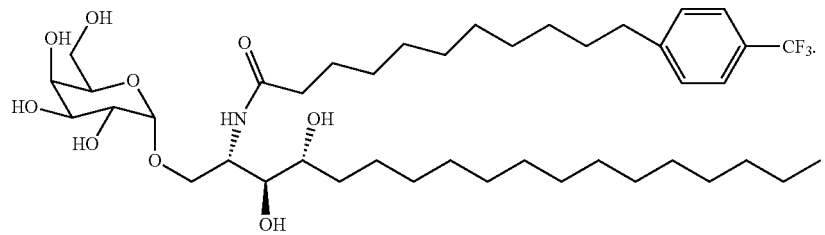 [SMILES: CCCCCCCCCCCCCC[C@@H](O)[C@@H](O)[C@H](COC1OC(CO)C(O)C(O)C1O)NC(=O)CCCCCCCCCCc1ccc(C(F)(F)F)cc1]

formula (6) (designated as 7DW8-6 in Li et al., and designated as formula 108 in U.S. Pat. No. 7,923,013)

Administration

In certain embodiments, a pharmaceutical composition comprising one or more species of live *Plasmodium* sporozoite-stage parasites is co-administered with a glycolipid adjuvant. In some embodiments, the co-administration is by the same or a different route of administration. For example, a pharmaceutical composition comprising one or more species of live *Plasmodium* sporozoite-stage parasites administered by an intravenous, intramuscular, intradermal, or subcutaneous route can be co-administered with a glycolipid adjuvant administered by an intravenous, intramuscular, intradermal, or subcutaneous route. In a further embodiment, an antimalarial drug can be further co-administered by an intravenous, intramuscular, intradermal, or subcutaneous route.

In some embodiments, the co-administration is concurrent, e.g., as an admixture. In some embodiments, the co-administration is sequential. In certain embodiments, the time between sequential administration events is not greater than about one hour, not greater than about 30 minutes, not greater than about 15 minutes, not greater than about 10 minutes, or not greater than about 5 minutes between the administrations. In certain embodiments, the time between co-administration events is 0-60 minutes between administrations, 0-30 minutes between administrations, 0-15 minutes administrations, 0-10 minutes between administrations, or 0-5 minutes between administrations.

In certain embodiments, a pharmaceutical composition comprising one or more species of live *Plasmodium* sporozoite-stage parasites is co-administered with one or more glycolipid adjuvants and additionally in the presence of an antimalarial drug at sufficient concentration in the bloodstream of the host to prevent the signs, symptoms or pathology of malaria upon subsequent exposure to pathogenic parasites. In other embodiments, a pharmaceutical composition comprising one or more species of live *Plas-* *modium* sporozoite-stage parasites and a glycolipid adjuvant are administered on the same time course or administered on an overlapping time course relative to an antimalarial drug, i.e., the antimalarial drug is not co-administered. As described, in some embodiments, the antimalarial drug was previously administered such that the concentration of said drug in the bloodstream of said host is sufficient to prevent the clinical manifestations of malaria.

Pharmaceutical Compositions

In compiling the results of the experiments disclosed in Examples 1 through 3, a combined 13% of BALB/c mice inoculated with radiation attenuated *P. yoelii* sporozoites (irr PySPZ) were protected from subsequent challenge by immunization with one dose administered IV. This level of protection improved to 75% when 7DW8-5 (formula (5)) was first delivered to the subject mice by intraperitoneal (IP) injection followed by the suboptimal IV dose of radiation attenuated Py sporozoites. These data show that 7DW8-5, administered distally and IP, can reduce the number of doses required to confer protection.

TABLE 1

Summary of experiments described in Examples 1-3

| Regimen | protected/ challenged | percent protected |
|---|---|---|
| irr PySPZ delivered IV | 4/30 | 13% |
| irr PySPZ delivered IV + 7DW8-5 delivered IP | 30/40 | 75% |
| 7DW8-5 delivered IP | 0/15 | 0% |
| Infectivity controls | 0/23 | 0% |

While *P. yoelii* is a species of *Plasmodium* with a mouse host range, it is widely used and generally considered a predictive model of the behavior of human host range *Plasmodium* by those skilled in the art (See e.g. Khan, Z. M. and J. P. Vanderberg (1991) *Role of Host Cellular Response in Differential Susceptibility of Nonimmunized BALB/c Mice to Plasmodium berghei and Plasmodium yoelii Sporozoites.* Infect. and Immun. 59(8):2529-2534). *Plasmodium* species with human host range include *P. falciparum*, *P. vivax*, *P. ovale*, *P. knowlesi*, and *P. malariae*.

All of the references cited above, as well as all references cited therein, are incorporated herein by reference in their entireties.

EXAMPLES

Example 1

Immunization of BALB/c Mice with Fresh Unpurified Radiation Attenuated *Plasmodium yoelii* Sporozoites To determine if the adjuvant 7DW8-5 could decrease the number of doses of irr PySPZ required to confer protection, a suboptimal dosing regimen was performed. irr PySPZ (17NXL) were dissected from the salivary glands of *A. stephensi* mosquitoes and injected intravenously (IV) into BALB/c mice as a single dose of either of $5\times10^4$ or $1\times10^4$ sporozoites. Two µg of 7DW8-5 was concurrently administered intraperitoneally (IP) in some mice. Fourteen days later, mice were challenged with 100 non-irradiated pathogenic *P. yoelii* sporozoites. Protection was assessed by Giemsa-stained blood smears and was defined as the complete absence of parasitemia 7 and 14 days post infection.

In the absence of adjuvant, 0/5 mice and 1/5 mice that received $5\times10^4$ and $1\times10^4$ respectively were protected. When administered with adjuvant, 3/5 and 4/5 mice were protected, respectively. Adjuvant alone provided no protection, indicating an antigen specific response.

TABLE 2

Example #1. Immunization with fresh, unpurified radiation attenuated Py sporozoites

| # of BALB/c mice | fresh, unpurified irr PySPZ IV | 2 µg 7DW8-5 IP | #protected/ #Challenged |
|---|---|---|---|
| 5 | $5 \times 10^4$ | − | 0/5 |
| 5 | $5 \times 10^4$ | + | 3/5 |
| 5 | $1 \times 10^4$ | − | 1/5 |
| 5 | $1 \times 10^4$ | + | 4/5 |
| 5 | — | + | 0/5 |
| 5 | Infectivity controls | − | 0/5 |

Example 2

Immunization of BALB/c Mice with Fresh Unpurified Radiation Attenuated Py Sporozoites A second experiment was performed to confirm the results shown in Example 1. Using the same method as Example 1, a single dose of $1\times10^4$ irr PySPZ did not protect any of 10 mice, but when combined with adjuvant protected 7 of 10 mice. Again, adjuvant in the absence of antigen had no effect.

TABLE 3

Example #2. Immunization with fresh, unpurified radiation attenuated Py sporozoites

| # of BALB/c mice | fresh, unpurified irr PySPZ IV | 2 µg 7DW8-5 IP | #protected/ #challenged |
|---|---|---|---|
| 10 | $1 \times 10^4$ | − | 0/10 |
| 10 | $1 \times 10^4$ | + | 7/10 |
| 5 | — | + | 0/5 |
| 10 | Infectivity control | − | 0/10 |

Example 3

Immunization of BALB/c Mice with Fresh Purified Radiation Attenuated Py Sporozoites Using the single dose methodology of Example 1 with radiation attenuated Py sporozoites that have been purified using the purification procedure disclosed in Sim et al. (U.S. Pat. No. 8,043,625, incorporated in its entirety herein by reference) a third experiment was performed. Using $1\times10^4$ purified sporozoites administered IV in a single dose, 3 out of 10 mice were protected, whereas 7 of 10 mice were protected when the adjuvant was concurrently administered IP.

TABLE 4

Example #3. Immunization with purified radiation attenuated Py sporozoites

| number of BALB/c mice | fresh irr PySPZ IV | 2 µg 7DW8-5 IP | # protected/ # challenged |
|---|---|---|---|
| 10 | $1 \times 10^4$ unpurified | + | 9/0 |
| 10 | $1 \times 10^4$ purified | − | 3/10 |
| 10 | $1 \times 10^4$ purified | + | 7/10 |
| 5 | — | + | 0/5 |
| 8 | Infectivity controls | − | 0/8 |

Example 4

Rechallenge—Longevity of Protection

Fifteen weeks after their first challenge with fresh, infectious *P. yoelii* sporozoites, the mice that had received a single dose of $10^4$ irradiated *P. yoelii* sporozoites with or without concurrent administration of adjuvant IP and were protected in Experiment #1 were re-challenged by the intravenous inoculation of 100 fresh, pathogenic *P. yoelii* sporozoites. Surprisingly, all four mice that had been protected after a single inoculation of $10^4$ irradiated *P. yoelii* sporozoites with concurrent distal IP administration of adjuvant were protected upon re-challenge. The single mouse that had been protected after administration of $10^4$ irradiated *P. yoelii* sporozoites without adjuvant was not protected upon re-challenge. All five infectivity controls developed parasitemia (see Table 5). The protection after a single inoculation of $10^4$ irradiated *P. yoelii* sporozoites with 2 µg 7DW8-5 adjuvant was solidly sustained for at least 15 weeks.

TABLE 5

Example #4 - Rechallenge Experiment. Immunization with fresh, unpurified radiation attenuated Py sporozoites

| #of BALB/c mice | fresh, unpurified irr PySPZ IV | 2 µg 7DW8-5 IP | First Challenge # protected/ # re-challenged | Re-challenge 101 days (15 weeks) after 1st challenge # protected/ # re-challenged |
|---|---|---|---|---|
| 5 | 1 × 10⁴ | − | 1/5 | 0/1 |
| 5 | 1 × 10⁴ | + | 4 | 4/4 |
| 5 | — | + | 0/5 | |
| 5 | Infectivity controls | − | 0/5 | |
| 5 | Infectivity controls | − | | 0/5 |

Example 5

Single Dose Optimization

To determine the optimal single dose of attenuated sporozoites (in conjunction with 7DW8-5 concurrently administered distally IP) that confers protection by the IV route, mice were injected IV with 0, 2500, 5000, 10,000 and 20,000 sporozoites. Two µg of 7DW8-5 were injected IP. As shown in Table 6, 80% protection was achieved in the group of mice receiving 10,000 sporozoites.

TABLE 6

Example #5 - Dose Optimization Experiment. Immunization with fresh, unpurified radiation attenuated Py sporozoites

| number of BALB/c mice | fresh, unpurified irr PySPZ IV | 2 µg 7DW8-5 IP | # protected/ # challenged |
|---|---|---|---|
| 5 | 0 | + | 0/5 |
| 5 | 0.25 × 10⁴ | + | 0/5 |
| 5 | 0.5 × 10⁴ | + | 2/5 |
| 5 | 1 × 10⁴ | + | 4/5 |
| 5 | 2 × 10⁴ | + | 1/5 |
| 5 | Infectivity controls | − | 0/5 |

Example 6

Two Dose Optimization—Intradermal

To determine whether protective immunogenicity of attenuated sporozoites is maintained or enhanced in the presence of 7DW8-5, mice were immunized by intradermal (ID) injection alone, with 2 doses at 2-week intervals of 15,000, 10,000, 5,000 and 2,500 sporozoites and unlike Examples 1-5, 1 µg 7DW8-5 was mixed as a composition with sporozoites and the composition of adjuvant and sporozoites was delivered ID at the base of the tail. With 2 doses of 15,000 sporozoites in the presence of adjuvant 100% of the mice were protected, and at lower doses of sporozoites 60-80% of the mice were protected. In the absence of adjuvant, only 40% of mice receiving 2 doses of 15,000 sporozoites were protected. This demonstrates that 7DW8-5 is compatible with live attenuated *Plasmodium* sporozoites, and the composition enhances the protection provided by attenuated sporozoites alone.

TABLE 7

Example # 6 - Two dose Intradermal Immunization. Immunization with fresh, unpurified radiation attenuated Py sporozoites ID co-administered with adjuvant at base of tail.

| number of BALB/c mice | fresh, unpurified irr PySPZ ID | 1 µg 7DW8-5 per mouse | # doses at 2-week intervals | # protected/ # challenged |
|---|---|---|---|---|
| 5 | 1.5 × 10⁴ | − | two | 2/5 |
| 5 | 1.5 × 10⁴ | + | two | 5/5 |
| 5 | 1.0 × 10⁴ | + | two | 3/5 |
| 5 | 0.5 × 10⁴ | + | two | 4/5 |
| 5 | 0.25 × 10⁴ | + | two | 3/5 |
| 5 | 0 | + | two | 0/5 |
| 8 | Infectivity controls | | | 0/8 |

Example 7

Single Dose Immunization Intradermal

Protection conferred by a single dose of a composition of 1 µg 7DW8-5 adjuvant and varying amounts of sporozoites delivered ID was measured. For this 15,000 and 30,000 sporozoites were administered to mice ID as described above. These doses were partially protective at 60% and 40% respectively.

TABLE 8

Example #7 - Single dose Intradermal Immunization Experiment. Immunization with fresh, unpurified radiation attenuated Py sporozoites ID co-administered with adjuvant at base of tail

| number of BALB/c mice | fresh, unpurified irr PySPZ ID | 1 µg 7DW8-5 per mouse | # doses at 2-week intervals | # protected/ # challenged |
|---|---|---|---|---|
| 5 | 1.5 × 10⁴ | + | one | 3/5 |
| 5 | 3 × 10⁴ | + | one | 2/5 |
| 5 | Infectivity controls | − | two | 0/5 |

Example 8

Single Dose Purified Sporozoites ID

The next step in development was to assess purified irr PySPZ BALB/c/mice were immunized with irr PySPZ purified as described, in the presence or absence of 7DW8-5 adjuvant. Three out of five (60%) mice were protected after immunization with 30,000 purified irr PySPZ mixed with 1 µg adjuvant administered ID at the base of the tail, and none were protected in the absence of adjuvant. No protection was observed in mice receiving adjuvant alone.

In the foregoing, the present invention has been described with reference to suitable embodiments, but these embodiments are only for purposes of understanding the invention and various alterations or modifications are possible.

What is claimed is:

1. A method of reducing the risk of malaria in a human host exposed to pathogenic *Plasmodium* species parasites, comprising administration of one or more doses of a pharmaceutical composition to said host prior to said exposure; wherein said pharmaceutical composition comprises (i) one or more species of live attenuated *Plasmodium* sporozoite-stage parasites, and (ii) an excipient; and wherein said pharmaceutical composition is co-administered with a glycolipid adjuvant represented by the structure of formula 1;

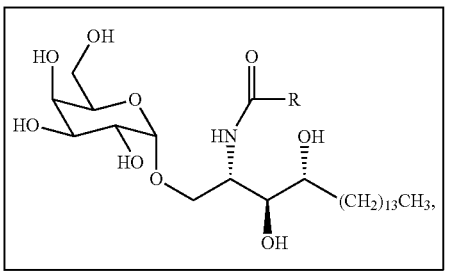
(1)

wherein R is R=$(CH_2)_{10}$Ph(p-F).

2. The method of claim 1, wherein said one or more doses comprise no more than 150,000 sporozoites.

3. The method of claim 2, wherein said one or more doses comprise no more than 50,000 sporozoites.

4. The method of claim 3, wherein said one or more doses comprise no more than 25,000 sporozoites.

5. The method of claim 1, wherein no more than 3 doses are administered.

6. The method of claim 5, wherein no more than 2 doses are administered.

7. The method of claim 6, wherein no more than 1 dose is administered.

8. The method of claim 1, wherein said species are selected from the group consisting of: *P. falciparum, P. vivax, P. ovale, P. knowlesi*, and *P. malariae*.

9. The method of claim 1, wherein said species comprises *P. falciparum*.

10. The method of claim 1, wherein said pharmaceutical composition is administered by an intravenous, intramuscular, intradermal, or subcutaneous route.

11. The method of claim 10, wherein said pharmaceutical composition is administered by an intravenous route.

12. The method of claim 1, wherein said glycolipid adjuvant is administered by an intravenous, intramuscular, intradermal, or subcutaneous route.

13. The method of claim 1, wherein the co-administration is sequential.

14. The method of claim 1, wherein the co-administration is concurrent.

15. The method of claim 14, wherein said glycolipid adjuvant and said pharmaceutical composition are admixed prior to co-administration.

16. The method of claim 1, wherein said pharmaceutical composition and said glycolipid adjuvant are co-administered by different routes of administration.

* * * * *